United States Patent [19]
Roby et al.

[11] Patent Number: 5,889,075
[45] Date of Patent: Mar. 30, 1999

[54] IRRADIATED SURGICAL SUTURE AND METHOD FOR MAKING SAME

[75] Inventors: Mark Roby, Killingworth; Anthony Arena, Stratford, both of Conn.

[73] Assignee: United States Surgical Corporation, Norwalk, Conn.

[21] Appl. No.: 948,701

[22] Filed: Oct. 10, 1997

[51] Int. Cl.$^6$ ................................ C08J 3/28; A61B 17/04
[52] U.S. Cl. ................ 522/87; 522/88; 522/135; 522/178; 606/228; 606/230; 606/231; 378/51; 378/64
[58] Field of Search ................ 522/87, 88, 135, 522/178; 606/228, 230, 231; 378/51, 64

[56] References Cited

U.S. PATENT DOCUMENTS

| | | | |
|---|---|---|---|
| 2,844,559 | 7/1958 | Parker . | |
| 3,451,394 | 6/1969 | Bechtol et al. . | |
| 3,636,956 | 1/1972 | Schneider . | |
| 3,838,093 | 9/1974 | Owston . | |
| 3,867,190 | 2/1975 | Schmitt et al. . | |
| 3,943,933 | 3/1976 | Gertzman . | |
| 4,067,836 | 1/1978 | Potts et al. . | |
| 4,093,576 | 6/1978 | deWijn . | |
| 4,373,217 | 2/1983 | Draenert . | |
| 4,435,590 | 3/1984 | Shalaby et al. | 560/61 |
| 4,496,446 | 1/1985 | Ritter et al. . | |
| 4,650,488 | 3/1987 | Bays et al. | 623/12 |
| 4,842,603 | 6/1989 | Draenert | 623/16 |
| 4,865,602 | 9/1989 | Smestad et al. | 623/16 |
| 4,898,734 | 2/1990 | Mathiowitz et al. | 424/426 |
| 4,950,516 | 8/1990 | Schwab | 428/36.92 |
| 4,969,906 | 11/1990 | Kronman | 623/16 |
| 4,997,446 | 3/1991 | Thoma | 623/16 |
| 5,216,050 | 6/1993 | Sinclair | 524/108 |
| 5,342,395 | 8/1994 | Jarrett et al. | 606/219 |
| 5,485,496 | 1/1996 | Lee et al. | 378/64 |
| 5,540,876 | 7/1996 | Larson et al. | 264/479 |

FOREIGN PATENT DOCUMENTS

WO8700419  1/1987  WIPO .

OTHER PUBLICATIONS

Effect of a combined gamma irradiation and parylene plasma treatment on the Hydrolytic degradation of synthetic biodegradable sutures; Journal of Biomedical Materials Research, vol. 27, pp. 1425–1441; 1993 John Wiley & Sons, Inc.

*Primary Examiner*—Nathan M. Nutter

[57] ABSTRACT

A surgical suture fabricated from a copolymer containing dioxanone, trimethylene carbonate and glycolide is treated with gamma radiation to enhance bioabsorbability without adversely effecting handling properties.

17 Claims, No Drawings

IRRADIATED SURGICAL SUTURE AND METHOD FOR MAKING SAME

BACKGROUND

1. Technical Field

The disclosure herein relates to a surgical suture, and in particular to a surgical suture which has been subjected to radiation treatment.

2. Background of Related Art

Implantable surgical devices such as surgical fasteners, clips, staples, and sutures are typically employed in surgical procedures to hold body tissue together to promote the healing and joining of the tissue. Such surgical devices are often made from synthetic bioabsorbable polymers. The advantage of bioabsorbable devices is that, once implanted, they do not need to be removed by a separate surgical operation since they are degraded and absorbed by the body. Ideally, the surgical device maintains its strength for as long as it takes the body tissues to heal. Thereafter, the device should rapidly degrade and disappear.

In various applications the body tissue heals much faster than the suture implanted therein is absorbed. In such cases, the suture remains in the body tissue longer than is necessary. Accordingly, it would be advantageous to treat the suture so that it degrades faster, without adversely affecting the mechanical properties of the suture.

U.S. Pat. No. 4,496,446 discloses modifying the absorption rate of anastomosis rings by the inclusion of certain filler materials in the ring, pre-treatment of the ring with hot water or steam, and subjecting the ring to gamma radiation. U.S. Pat. No. 4,435,590 discloses that exposure of sutures to radiation leads to distinct degradation in mechanical properties and to clinically unacceptable in vivo strength retention. Thus, those skilled in the art would not expect a treatment that includes radiating the suture to provide an acceptable product.

It would be desirable to provide a suture treatment that enhances absorption rate while not adversely affecting the desired physical qualities of the suture.

SUMMARY

A method is provided herein for treating a surgical suture to enhance its bioabsorbability. The surgical suture is preferably fabricated from a terpolymer of glycolide, dioxanone and trimethylene carbonate. In particularly useful embodiments, the suture is made from a block copolymer containing glycolide, dioxanone and trimethylene carbonate such as, for example, a block copolymer wherein the center block is a p-dioxanone/trimethylene carbonate copolymer and the two end blocks are p-dioxanone/glycolide copolymer. The surgical suture is exposed to gamma radiation in an amount ranging from about 2 Mrad to about 12 Mrad. Various sizes of monofilament or multifilament sutures can be treated in this manner to enhance the rate at which the suture is absorbed, but, quite surprisingly, without any significant adverse effect on the physical properties of the suture.

DETAILED DESCRIPTION OF THE PREFERRED EMBODIMENTS

The method described herein relates to the irradiation of a suture fabricated from synthetic bioabsorbable polymer to increase the rate of absorption of the suture in the body.

Suture sizes referred to below are USP synthetic suture sizes as listed in the United States Pharmacopeia (USP XXII, page 1307).

The suture can be a monofilament or multifilament suture and is preferably fabricated from a terpolymer of glycolide, p-dioxanone, and trimethylene carbonate. Particularly useful herein are substances made from block copolymers of glycolide, dioxanone and trimethylene carbonate.

Suitable block copolymers have two specific types of blocks, a "A" block having a proportion of glycolic acid ester units as the predominant component thereof and a "B" block comprising 1,3 dioxane-2-one randomly copolymerized with 1,4 dioxane-2-one. Such copolymers can advantageously be formed into fibers and irradiated to provide relatively fast absorbing sutures with good physical properties.

The preferred block copolymer compositions for use in making sutures to be irradiated include an A block formed from a copolymer which has glycolide as the predominant component thereof. That is glycolide comprises at least 50 mole percent of the first block. Preferably, glycolide comprises at least about 60 mole percent of the first block and most preferably at least about 95 mole percent glycolide. The glycolide may be copolymerized with any monomer which provides an absorbable copolymer to form the A block. Such monomers include but are not limited to lactide, trimethylene carbonate, p-diohanone, and epsilon-caprolactone. The copolymers of glycolide which form the first block can be random or block copolymers and can be synthesized by known methods. See, for example, U.S. Pat. Nos. 4,653,497; 4,838,267; 4,429,080; 4,665,730; and 4,788,979 the disclosures of which are incorporated herein by reference.

The B block of the preferred copolymers has 1,4-dioxane-2-one and 1,3-dioxane-2-one linkages. Preferably 1,4-dioxane-2-one comprises from about 20 mole percent to about 80 mole percent, and more preferably from about 35 mole percent to about 65 mole percent of the B block. Most preferably, 1,4-dioxane-2-one comprises at least about 35 mole percent of the B block, the remainder of the block comprising 1,3-dioxane-2-one. Copolymers of 1,3-dioxane-2-one and 1,4-dioxane-2-one having an inherent Viscosity of from about 0.5 to about 2 dl/g measured at 30° C. and a concentration of 0.25 g/dl in chloroform or hexafluoroisopropanol (HFIP) may generally be used as the second block.

The block copolymers can be prepared by preparing the individual polymers which make up the blocks and then copolymerizing these polymers to form a block or graft copolymer. Alternatively, a pre-polymer having 1,4-dioxane-2-one and 1,3-dioxane-2-one linkages may be prepared in a reactor and then the monomers needed to form the other block or blocks are added directly to the reactor to thereby form the block copolymer. In one embodiment the polymerization reaction used in the formation of the above mentioned pre-polymer is stopped short of completion, leaving residual 1,4-dioxane-2-one. Then monomers needed to form the block or blocks are added directly to the reactor vessel to react the residual 1,4-dioxane-2-one and the pre-polymer to form block copolymers having 1,4-dioxane-2-one linkages in each block.

In forming the preferred block copolymers from which the sutures are made, the A (predominately glycolide) block may be present in an amount from about 50 to about 80 percent by weight based on the weight of the final block copolymer. The B (random copolymer) block may be present in an amount from about 20 to about 50 weight percent based on the weight of the final block copolymer. Preferably, the R block comprises between about 60 and about 70 weight percent of the block copolymer. In a particularly useful embodiment, the A block comprises about 65 weight percent and the B block comprises about 35 weight percent of the final block copolymer. The copolymers of the present invention have a molecular weight such that their inherent viscosity is from about 0.5 to about 2.0 dl/g, and preferably from about 1 to about 1.40 dl/g measured at 30° C. at a concentration of 0.25 g/dl in chloroform or HFIP.

Each A and B block may comprise a single type of recurring monomeric unit. Alternatively, each block may comprise more than one type of recurring monomeric unit randomly distributed throughout each block. The block copolymers used to form the sutures may have repeating block units such as AB, ABA, ABAB, ABABA, BABA, etc.; with ABA being preferred.

A particularly useful suture for use herein is BIOSYN™ sutures available from United States Surgical Corporation, Norwalk, Conn.

If the suture is multifilament it can be manufactured by any of the known methods for combining multiple strands, such as braiding, twisting, and the like. Prior or subsequent to the irradiation treatment the suture can be coated or filled with various coating and/or filling agents to improve handling characteristics and storage stability. Such agents are disclosed, for example, in U.S. Pat. Nos. 5,306,289, 5,269,808 and 5,226,912, all of which are incorporated by reference.

The irradiation treatment is performed by subjecting the suture to gamma-radiation from, for example, a cobalt-60 source. The total dose rate can range about 2 to about 12, preferably from about 5 to 8 Mrad. The suture is preferably exposed to the radiation while under vacuum or in an atmosphere from which oxygen is excluded. The suture is preferably kept at about temperature while being irradiated. The irradiation treatment results in a suture with enhanced bioabsorbability as illustrated by the examples given below.

Advantageously, irradiation of sutures of the preferred block copolymer compositions exhibit strength retention and mass loss profiles similar to the profiles of gut sutures. However, because they are synthetic absorbable sutures, the irradiated sutures do not exhibit any of the perceived disadvantages (e.g., fraying, inconsistent strength, etc.) typically associated with gut sutures.

EXAMPLE 1

Samples of size 0 BIOSYN™ sutures were divided into three groups. The first group received no irradiation. The second group received one dose of irradiation, the third group received two doses of irradiation.

The irradiation was conducted by exposing the suture to the gamma radiation from a cobalt-60 source for 2.7 hrs. for a single dose of 2.5–4 Mrad. The irradiation was conducted at ambient temperature. Sutures irradiated a second time received two identical doses of gamma radiation as described above.

Knotted suture loops were implanted subcutaneously into 18 rats, each animal receiving 2 non-irradiated, 2 once irradiated, and 2 twice irradiated sutures for a total of six sutures. Modified U.S.P. knots were tied in each suture using sterile technique. Suture loops were formed around glass mandrels (diameter=7 mm) and secured with a surgeon's knot tied square (2=1). The ears on the knot were cut to be 25 mm long. The loop was removed from the mandrel and placed in an appropriately labeled sterile Petri dish until implantation. The suture samples from six rats were harvested at each of three analysis intervals of one, two and three weeks. Another group of knotted suture loops was not implanted to provide data for initial strength determination (week 0).

The knotted suture loops were tested for strength on an Instron Universal Testing Machine (Model 1123) to determine the breaking strength of each knotted suture loop, and the mean breaking strength was calculated. The results the in vivo testing are shown in Table I.

TABLE I

| (Size 0 suture mean breaking strength, kg.) | | | |
|---|---|---|---|
| Implant Age | Unirradiated | One Dose | Two Doses |
| 0 weeks | 5.51 | 4.69 | 4.33 |
| 1 week | 4.69 | 3.44 | 2.80 |
| 2 weeks | 3.60 | 2.22 | 1.12 |
| 3 weeks | 2.49 | 0.68 | 0.20 |

These results show that the irradiated sutures had an enhanced rate of absorption. However, at week 0 the irradiated sutures were within the acceptable strength requirements for absorbable sutures.

EXAMPLE 2

Samples of size 3/0 BIOSYN™ monofilament sutures of the same composition as those in Example 1 were divided into three groups. The first group received no irradiation. The second group received one dose of irradiation, the third group received two doses of irradiation. The radiation treatment was conducted in a manner similar to that of Example 1.

Sutures knotted into loops in the manner previously described were implanted subcutaneously into 18 rats, each animal receiving 2 non-irradiated, 2 once irradiated, and 2 twice irradiated sutures for a total of six sutures. The suture samples from six rats were harvested at each of three analysis intervals of one, two and three weeks. Another group of knotted suture loops was not implanted to provide data for initial strength determination (week 0).

The knotted suture loops were tested for strength on an Instron Universal Testing Machine (Model 1123) to determine the breaking strength of each knotted suture loop, and the mean breaking strength was calculated. The results of the in vivo testing are shown in Table II.

TABLE II

| (Size 3/0 suture mean breaking strength, kg.) | | | |
|---|---|---|---|
| Implant Age | Unirradiated | One Dose | Two Doses |
| 0 weeks | 2.45 | 2.06 | 1.66 |
| 1 week | 2.06 | 1.37 | 0.84 |
| 2 weeks | 1.69 | 1.02 | 0.65 |
| 3 weeks | 1.13 | 0.39 | 0.15 |

These results show that the irradiated sutures had an enhanced rate of absorption, but maintained acceptable initial strength.

Example 3

Samples of size 5/0 BIOSYN™ monofilament sutures of the same composition as those in Example 1 were divided into three groups. The first group received no irradiation. The second group received one dose of irradiation, the third group received two doses of irradiation. The radiation treatment was conducted in a manner similar to that of Example 1.

Sutures knotted into loops in the manner previously described were implanted subcutaneously into 18 rats, each animal receiving 2 non-irradiated, 2 once irradiated, and 2 twice irradiated sutures for a total of six sutures. The suture samples from six rats were harvested at each of three analysis interuals of one, two and three weeks. Another group of knotted suture loops was not implanted to provide data for initial strength determination (week 0).

The knotted suture loops were tested for strength on an Instron Universal Testing Machine (Model 1123) to determine the breaking strength of each knotted suture loop, and the mean breaking strength was calculated. The results of the in vivo testing are shown in Table III.

TABLE III (Size 5/0 suture mean breaking strength, kg.)

| Implant Age | Unirradiated | One Dose | Two Doses |
|---|---|---|---|
| 0 weeks | 1.00 | 0.55 | 0.25 |
| 1 week | 0.83 | 0.37 | 0.25 |
| 2 weeks | 0.65 | 0.34 | 0.23 |
| 3 weeks | 0.44 | 0.17 | 0.07 |

These results show that the irradiated sutures had an enhanced rate of absorption. However, the physical characteristics of the suture were not significantly adversely affected by irradiation.

It will be understood that various modifications may be made to the embodiments disclosed herein. Therefore, the above description should not be construed as limiting, but merely as exemplification of preferred embodiments. Those skilled in the art will envision many other embodiments within the scope and spirit of the claims appended hereto.

What is claimed is:

1. A method for treating a surgical suture to enhance the bioabsorbability thereof, comprising the steps of:
   a) providing a bioabsorbable surgical suture fabricated from a terpolymer having repeating units derived from p-dioxanone, trimethylene carbonate and glycolide;
   b) exposing the surgical suture at ambient temperature to gamma radiation at a first dosage ranging from about 2 Mrad to about 12 Mrad.

2. The method of claim 1 wherein said bioabsorbable surgical suture is a monofilament suture.

3. The method of claim 1 wherein the suture is a multifilament suture.

4. The method of claim 1 wherein step (a) comprises providing a suture made from a block copolymer.

5. The method of claim 4 wherein step (a) comprises providing a suture made from a triblock copolymer having a center block with randomly combined p-dioxanone and trimethylene carbonate and end blocks with a predominant amount of glycolide.

6. The method of claim 5 wherein the end blocks comprise randomly combined repeating units derived from glycolide and p-diohanone.

7. The method of claim 1 further comprising the step of exposing the suture to gamma radiation a second time at a second dosage, wherein the second dosage is equal to the first dosage.

8. A suture comprising a fiber of gamma irradiated block copolymer having repeating units derived from p-dioxanone, trimethylene carbonate and glycolide.

9. The suture of claim 8, wherein the surgical suture loses at least about ⅔ of its initial strength after being implanted for three weeks in body tissue.

10. The suture of claim 8 wherein the block copolymer is a triblock copolymer.

11. The suture of claim 10 wherein the triblock copolymer has a center block containing a random combination of units derived from p-diohanone and trimethylene carbonate.

12. The suture of claim 10 wherein the end blocks comprise randomly combined repeating units derived from glycolide and p-dioxanone.

13. The suture of claim 8 wherein the fiber is gamma irradiated at a dose ranging from about 2 Mrad to about 5 Mrad.

14. The suture of claim 8 wherein the fiber is gamma irradiated twice.

15. A monofilament suture in accordance with claim 8.

16. A monofilament suture in accordance with claim 11.

17. The suture of claim 8 wherein the block copolymer contains a first block that is a copolymer of p-dioxanone and trimethylene carbonate and the second block that is a copolymer of glycolide and p-dioxanone.

* * * * *